(12) United States Patent
Sun et al.

(10) Patent No.: US 8,258,155 B2
(45) Date of Patent: Sep. 4, 2012

(54) QUININE SULFATE/BISULFATE SOLID COMPLEX; METHODS OF MAKING; AND METHODS OF USE THEREOF

(75) Inventors: Tong Sun, Marlton, NJ (US); Shawn Watson, Cherry Hill, NJ (US); Wei Lai, West Lafayette, IN (US); Stephan D. Parent, West Lafayette, IN (US)

(73) Assignee: Mutual Pharmaceutical Company, Inc., Philadelphia, PA (US)

( * ) Notice: Subject to any disclaimer, the term of this patent is extended or adjusted under 35 U.S.C. 154(b) by 510 days.

(21) Appl. No.: 12/491,311

(22) Filed: Jun. 25, 2009

(65) Prior Publication Data

US 2009/0326005 A1 Dec. 31, 2009

Related U.S. Application Data

(60) Provisional application No. 61/076,780, filed on Jun. 30, 2008.

(51) Int. Cl.
*C07D 215/38* (2006.01)
*A61K 31/04* (2006.01)

(52) U.S. Cl. ...................................... 514/312; 546/159

(58) Field of Classification Search .................. 546/159; 514/312

See application file for complete search history.

(56) References Cited

U.S. PATENT DOCUMENTS

| | | | |
|---|---|---|---|
| 501,066 | A | 7/1893 | Grimaux |
| 2002/0114844 | A1 | 8/2002 | Hanna et al. |
| 2004/0176335 | A1 | 9/2004 | Childs |
| 2005/0181041 | A1 | 8/2005 | Goldman |
| 2006/0243831 | A1 | 11/2006 | Gonzalez-Zugasti et al. |
| 2006/0263427 | A1 | 11/2006 | Roberts et al. |
| 2007/0026078 | A1 | 2/2007 | Almarsson et al. |
| 2007/0059356 | A1 | 3/2007 | Almarsson et al. |
| 2007/0088508 | A1 | 4/2007 | Childs |
| 2007/0212683 | A1 | 9/2007 | Connelly |
| 2009/0163540 | A1 | 6/2009 | Sun et al. |

FOREIGN PATENT DOCUMENTS

| | | |
|---|---|---|
| WO | 0238127 A2 | 5/2002 |
| WO | 2004/060347 A2 | 7/2004 |
| WO | 2004060347 A2 | 7/2004 |
| WO | 2004/078161 A1 | 9/2004 |
| WO | 2004/078163 A2 | 9/2004 |
| WO | 2005/089375 A2 | 9/2005 |
| WO | 2005089375 A2 | 9/2005 |

OTHER PUBLICATIONS

West, Solid State CHemistry and Its Applications, Wiley, New York, pp. 358,365, 1988.*
Byrn et al., Pharmaceutical Solids: A Strategic Approach to Regulatory Considerations, Pharmaceutical Research, vol. 12, No. 7, 1995, 945-954.
Glynis Davies, Changing the Salt, Changing the Drug, The Pharmaceutical Journal, vol. 266, No. 713, Mar. 10, 2001, pp. 322-323.
The Merck Index, Quinine sulfate dihydrate, 8151, 13th Edition, p. 1444, 1969.
Akasaka et al., "Investigations of Molecular Recognition Aspects Related to the Enantiomer Separation of 2-Methoxy-2-(1-naphthyl)propionic Acid Using Quinine Carbamate as Chiral Selector: An NMR and FT-IR Spectroscopic as Well as X-Ray Crystallographic Study", Chirality 17(9): 544-555 (2005).
Liu et al., "Effects of carboxylic acids on the microstructure and performance of titania nanocrystals", Chemical Engineering Journal 138(1-3): 596-601 (2008).
Balevicius et al., "Proton transfer in hydrogen-bonded pyridine/acid systems: the role of higher aggregation", Phys. Chem. Chem. Physics., 9: 3181-3189 (2007).
Trask et al., "Physical stability enhancement of theophylline via cocrystallization", International Journal of Pharmaceutics 320(1-2): 114-123 (2006).
International Search Report; International Application No. PCT/US2009/048556; International Filing Date Jun. 25, 2009; 9 pages.
Written Opinion of the International Searching Authority; International Application No. PCT/US2009/048556; International Filing Date Jun. 25, 2009; 4 pages.
Mendel, "An X-ray Study of the Quinine Molecule", Chemistry, 1955, pp. 132-134.
Quinine, The Merck Index, 13th Edition, O'Neil et al. (eds), Merck & Co., Inc., Whitehouse Station, NJ, 2001, p. 1444.

* cited by examiner

*Primary Examiner* — D M Seaman
(74) *Attorney, Agent, or Firm* — Cantor Colburn LLP

(57) ABSTRACT

Disclosed are new quinine sulfate/bisulfate solid complexes, methods of making the solid complexes as well as formulations prepared therefrom and uses thereof.

18 Claims, 4 Drawing Sheets

QUININE SULFATE/BISULFATE SOLID COMPLEX; METHODS OF MAKING; AND METHODS OF USE THEREOF

CROSS REFERENCE TO RELATED APPLICATION

This application claims the benefit of U.S. Provisional Application Ser. No. 61/076,780 filed Jun. 30, 2008, which is hereby incorporated by reference in its entirety.

BACKGROUND

Quinine(cinchonan-9-ol, 6'-methoxy-, (8α,9R)—) is an antiprotozoal and an antimyotonic, and is known for the treatment of malaria caused by *Plasmodium* species, the treatment of nocturnal recumbency leg muscle cramps, and the treatment of babesiosis caused by *Babesia microti*.

Various salts of quinine are known including quinine hydrochloride, and quinine sulfate. Crystalline quinine sulfate is known to exhibit low solubility in water at room temperature.

Different crystalline forms, non-crystalline forms, hydrates and solvates of an active agent can exhibit vastly different physical properties such as solubility, melting point, hardness, optical properties, dissolution, and the like. These differences such as varying dissolution can result in differences in the therapeutic activity. A thorough understanding of the various crystalline forms, non-crystalline forms, hydrates and solvates of an active agent is an important consideration in formulating the active agent, specifically when trying to achieve consistency of any resulting pharmaceutical product batch to batch.

There remains a need in the art for new solid forms of quinine having improved properties of solubility, stability, processability and the like.

SUMMARY

In one embodiment, a solid complex comprises quinine sulfate/bisulfate and a guest, wherein the guest is acetic acid or DL-tartaric acid.

In another embodiment, a composition comprises a solid complex comprising quinine sulfate/bisulfate and a guest, wherein the guest is acetic acid or DL-tartaric acid; and a pharmaceutically acceptable excipient.

In yet another embodiment, a method of preparing a solid complex comprises milling a combination of quinine sulfate and acetic acid to form quinine sulfate acetic acid solid complex.

In still another embodiment, a method of preparing a solid complex comprises preparing quinine sulfate acetic acid solid complex by liquid diffusion in ethyl acetate.

In another embodiment, a method of preparing a solid complex comprises crystallizing a solid complex from a solution containing quinine sulfate, a guest, and optionally a solvent system with optionally evaporating the solvent system from the solution, wherein the guest is DL-tartaric acid.

In yet another embodiment, a method of preparing a solid complex comprises adding an anti-solvent to a solution containing quinine sulfate, a guest, and optionally a solvent system; and precipitating a quinine sulfate solid complex, wherein the guest is acetic acid.

In one embodiment, a method of preparing a solid complex comprises dissolving quinine sulfate and tartaric acid in a lower alkyl alcohol with heating; allowing the solid complex to precipitate.

These and other embodiments, advantages and features of the present invention become clear when detailed description and examples are provided in subsequent sections.

DETAILED DESCRIPTION

Figure 1:
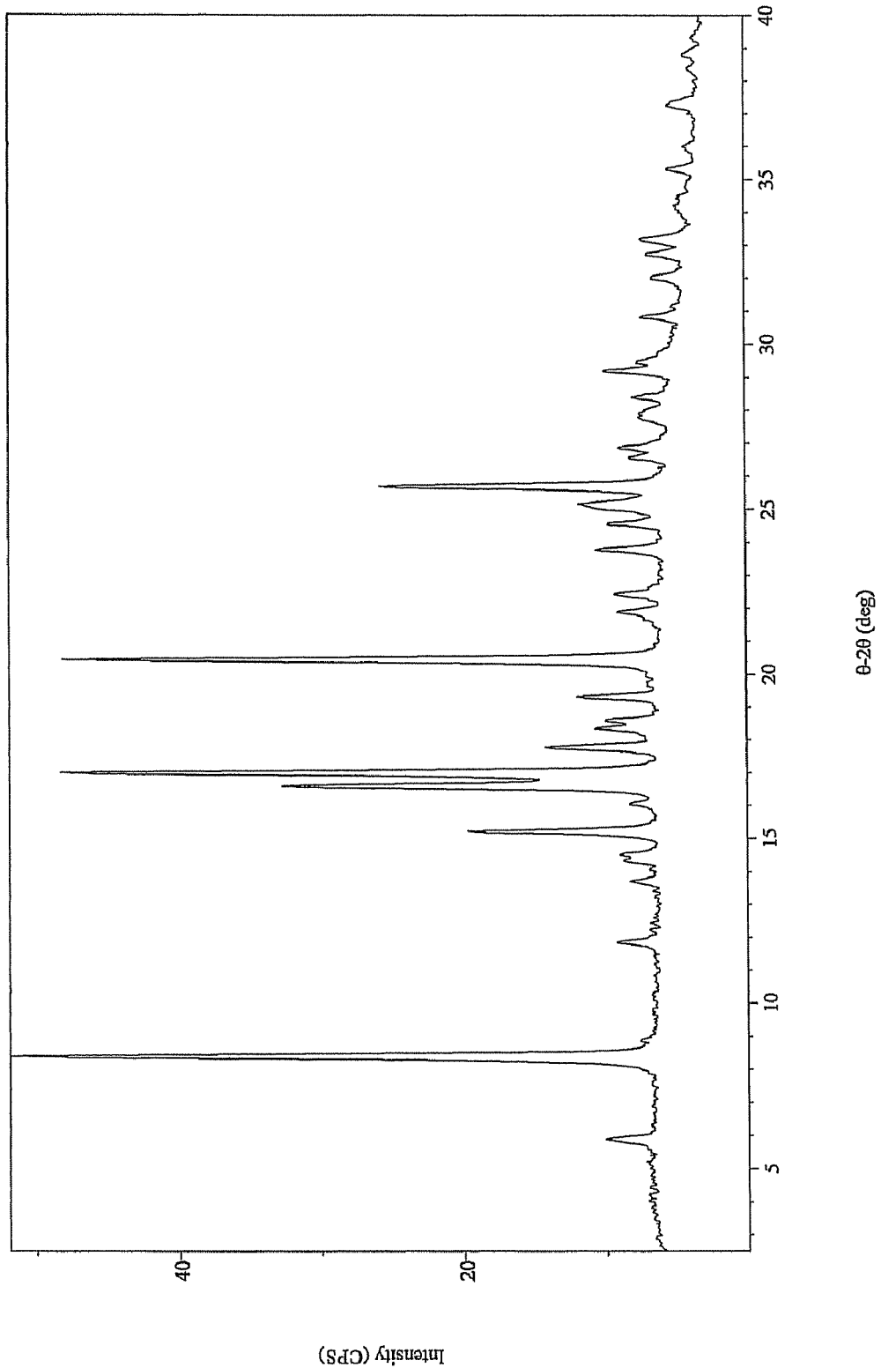
FIG. 1 illustrates XRPD pattern of quinine sulfate acetic acid solid complex.

Disclosed herein are novel quinine sulfate and quinine bisulfate solid complexes, methods of preparing the solid complexes, compositions prepared therefrom, and uses thereof. It has been unexpectedly discovered herein that quinine sulfate salts (e.g., quinine sulfate and quinine bisulfate) can exist as a solid complex (e.g., a co-crystal) with a guest molecule. Novel solid complexes disclosed herein include quinine sulfate acetic acid and quinine bisulfate tartaric acid.

"Solid complex" means a solid form containing quinine sulfate/bisulfate and an additional component ("guest") which interact with one another to result in a solid material having a different physicochemical property than the corresponding free quinine sulfate/bisulfate. The interactions between the quinine sulfate/bisulfate and the guest can be hydrogen bonding, van der Waals interactions, electrostatic interactions, hydrophobic interactions a combination thereof, and the like. Exemplary solid complexes include co-crystals (i.e. a crystalline supramolecular complex), single phase molecular dispersions, and the like. The properties can include solubility, melting point, spectroscopic, etc.

The solid complex may include one or more solvate or water molecules in the crystalline lattice (e.g., solvates or hydrates of co-crystals, or a co-crystal further comprising a solvent or water molecule).

"Quinine sulfate" and "quinine bisulfate" are inclusive of all crystalline forms including all polymorphs, non-crystalline forms, anhydrous forms, hydrates such as the dihydrate, and solvates unless specifically indicated otherwise. "Quinine sulfate/bisulfate" means quinine sulfate or quinine bisulfate. Specific polymorphs of quinine sulfate include those disclosed in co-pending Provisional Application Ser. No. 61/015,488, entitled "Quinine Sulfate Polymorphs, Processes of Preparing, Compositions and Uses Thereof" incorporated herein by reference in its entirety, specifically quinine sulfate polymorphs A, B, C, D, E, F, G, H, I, J, and K.

"Guest" means an organic acid, specifically acetic acid, gentisic acid, DL-mandelic acid, salicylic acid, or DL-tartaric acid.

The ratio of quinine sulfate/bisulfate to guest may be for example, 1:1, 1:1.5 and 1:2. In certain embodiments, the ratio is 1:1, 1:2, 1:3, 1:4, 1:5, 1:6, 1:7, 1:8, 1:9, or 1:10 quinine sulfate/bisulfate to guest. In other embodiments, the ratio is 1:1, 1:2, 1:3, 1:4, 1:5, 1:6, 1:7, 1:8, 1:9, or 1:10 guest to quinine sulfate/bisulfate.

The solid complexes can be physically distinguished from crystalline quinine sulfate/bisulfate using a variety of analytical tools and characterization methods, such as, for example, Raman spectroscopy, IR spectroscopy (IR, FT-IR), X-ray powder diffraction (XPRD) crystallography, X-ray crystallography, neutron diffraction, Synchrotron radiation, solid state NMR spectroscopy, differential scanning calorimetry (DSC), Thermogravimetric analysis (TGA), Thermogravimetric/infrared analysis (TG-IR), melting point, and heats of fusion.

The quinine sulfate/bisulfate solid complexes can be prepared using a variety of methods including antisolvent precipitation, slow cooling of a solution of quinine sulfate and guest, precipitation from a solution of quinine sulfate and guest at a constant temperature, seeding solutions of quinine sulfate and guest with optional cooling, slurrying and the like.

Exemplary methods for preparing solid complexes include mechanical and solvent processes. Exemplary mechanical processes include milling/grinding, and extrusion; and exemplary solvent processes include dissolving, partially dissolving (and optionally sonicating) in a common solvent, followed by solvent evaporation or spray-drying; or a combination thereof. Optionally, the process can be conducted under inert atmosphere (e.g., nitrogen, argon atmospheres).

In one embodiment, the quinine sulfate solid complex can be prepared by a milling process. The milling process generally involves grinding quinine sulfate and a guest in a mill, e.g., use of a ball mill, jet mill, impact mill, hammer mill, and the like. Optionally, the grinding can be performed with heating. The quinine sulfate or guest can be in crystalline form, solid non-crystalline form, liquid, or the like.

The milling process can include grinding for about 10 seconds to about 2 hours, specifically about 1 minute to about 90 minutes, and more specifically about 20 minutes to about 60 minutes.

The solvent process generally involves preparing a solution or suspension of quinine sulfate/bisulfate and guest in a solvent system followed by optional removal of the solvent. In the solution process, both quinine sulfate/bisulfate and guest are completely dissolved in the solvent system. In the suspension process, the quinine sulfate/bisulfate or guest can remain partially undissolved.

"Solvent system" means a single or a combination of two or more solvents.

Suitable solvents for preparing the quinine sulfate/bisulfate solid complex include those that do not adversely affect the stability of the quinine sulfate/bisulfate, guest or solid complex, and are preferably inert. Suitable solvents may be organic, aqueous, or a mixture thereof Suitable organic solvents may be aliphatic alcohols such as methanol (MeOH), ethanol (EtOH), n-propanol, isopropanol (IPA), n-butanol, tert-amyl alcohol (t-AmOH), tert-butyl alcohol, triflouroethanol, and 2-ethoxyethanol, particularly lower alkyl ($C_1$-$C_6$) alcohols; ethers such as tetrahydrofuran (THF), dioxane, methyl-tert-butyl ether, 1,2-dimethoxyethane (DME), and 2-methyl tetrahydrofuran; aliphatic ketones such as acetone, methyl ethyl ketone (MEK), and methyl isobutyl ketone; aliphatic carboxylic esters such as methyl acetate, ethyl acetate (EtOAc), and isopropyl acetate; aromatic hydrocarbons such as benzene, toluene, and xylene; aliphatic hydrocarbons such as hexane; aliphatic nitriles such as acetonitrile (MeCN) and propionitrile; chlorinated hydrocarbons such as dichloromethane (DCM), chloroform, and carbon tetrachloride; aliphatic sulfoxides such as dimethyl sulfoxide (DMSO); amides such as dimethylformamide (DMF) and dimethylacetamide (DMA); organic acids such as acetic acid; N-methyl-2-pyrrolidone; pyridine; and the like, as well as mixtures comprising at least one of the foregoing organic solvents. Certain solvents can be used as an anti-solvent to induce crystal formation from solution.

Optionally, the solution, prior to any solids formation, can be filtered to remove any undissolved solids, solid impurities and the like prior to removal of the solvent. Any filtration system and filtration techniques known in the art can be used.

In one embodiment, the solutions or suspensions can be seeded with the desired quinine sulfate solid complex.

In one embodiment, the solutions or suspensions can be sonicated.

In one embodiment, the solvent system of the solution or suspension of quinine sulfate/bisulfate, guest, and solvent system is removed slowly or rapidly. Rapid removal of the solvent system can be achieved in less than a minute by processes such as spray drying. Slow removal of the solvent system can be achieved in a minute or greater using methods such as evaporation under reduced pressure or evaporation at atmospheric pressure. Removal of the solvent system can be achieved with optional heating.

In one embodiment, a quinine sulfate acetic acid solid complex exhibits XRPD peak positions at 8.4, 15.2, 16.6, 17.0, 17.8, 19.3, 20.4, 23.8, 25.2, and 25.7±0.1 degree 2-theta. In another embodiment, a quinine sulfate acetic acid solid complex exhibits the XRPD peak positions in Table 4 below. In yet another embodiment, a quinine sulfate acetic acid solid complex exhibits an X-ray powder diffraction pattern which is substantially similar to FIG. 1. In another embodiment, a quinine sulfate acetic acid solid complex exhibits FT-Raman peaks at 1364, 1429, 1445, and 2954±4 $cm^{-1}$. In another embodiment, a quinine sulfate acetic acid solid complex exhibits FT-Raman peaks in Table 5 below. In yet another embodiment, a quinine sulfate acetic acid solid complex exhibits a FT-Raman spectrum which is substantially similar to FIG. 2.

In one embodiment, a solid complex of quinine sulfate is quinine sulfate acetic acid co-crystal, specifically quinine sulfate acetic acid co-crystal monohydrate (2quinine.$H_2SO_4$.$CH_3COOH$.$H_2O$). The quinine sulfate acetic acid co-crystal exhibits water solubility at room temperature of about 2 milligrams per milliliter.

Figure 3:
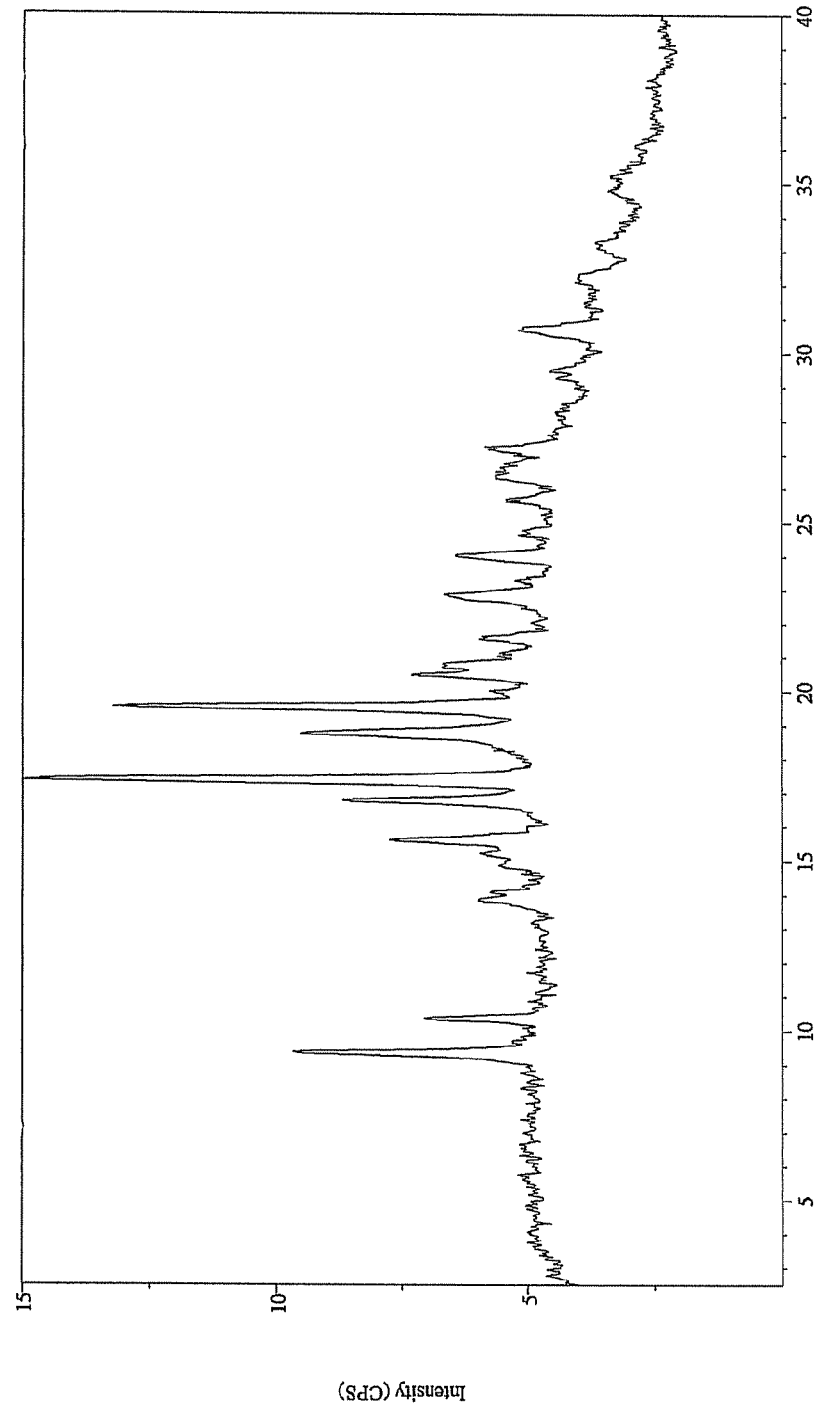
FIG. 3 illustrates XRPD pattern of quinine bisulfate tartaric acid solid complex.

In one embodiment, a quinine bisulfate tartaric acid solid complex exhibits XRPD peak positions at 9.4, 10.4, 13.8, 15.2, 15.6, 16.8, 17.4, 18.7, 19.5, and 20.5±0.1 degrees 2-theta. In another embodiment, a quinine bisulfate tartaric acid solid complex exhibits the XRPD peak positions in Table 9 below. In yet another embodiment, a quinine bisulfate tartaric acid solid complex exhibits an X-ray powder diffraction pattern which is substantially similar to FIG. 3. In another embodiment, a quinine bisulfate tartaric acid solid complex exhibits FT-Raman peaks at 767, 1386, 1431, and 1622±4 $cm^{-1}$. In another embodiment, a quinine bisulfate tartaric acid solid complex exhibits FT-Raman peaks in Table 10 below. In yet another embodiment, a quinine bisulfate tartaric acid solid complex exhibits a FT-Raman spectrum which is substantially similar to FIG. 4.

In another embodiment, a solid complex of quinine sulfate/bisulfate is quinine bisulfate tartaric acid co-crystal. The quinine bisulfate tartaric acid co-crystal exhibits solubility in water at room temperature of about 200 milligrams per milliliter.

Also disclosed herein are pharmaceutical compositions comprising the quinine sulfate/bisulfate solid complexes prepared herein.

Solid dosage forms for oral administration include, but are not limited to, capsules, tablets, powders, and granules. In such solid dosage forms, the solid complex may be admixed with one or more of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose, and acacia; (d) humectants, such as glycerol; (e) disintegrating agents, such as agar-agar, calcium carbonate, potato or tapioca starch, alginic acid, certain complex silicates, and sodium carbonate; (f solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, and combinations comprising one or more of the foregoing additives. For capsules and tablets, the dosage forms may also comprise buffering agents.

By "oral dosage form" is meant to include a unit dosage form for oral administration. An oral dosage form may optionally comprise a plurality of subunits such as, for example, microcapsules or microtablets. Multiple subunits may be packaged for administration in a single dose.

By "subunit" is meant to include a composition, mixture, particle, pellet, etc., that can provide an oral dosage form alone or when combined with other subunits.

The compositions can be immediate-release forms or controlled-release forms.

By "immediate-release" is meant a conventional or non-modified release in which greater then or equal to about 75% of the active agent is released within two hours of administration, specifically within one hour of administration.

By "controlled-release" is meant a dosage form in which the release of the active agent is controlled or modified over a period of time. Controlled can mean, for example, sustained-, delayed- or pulsed-release at a particular time. Alternatively, controlled can mean that the release of the active agent is extended for longer than it would be in an immediate-release dosage form, e.g., at least over several hours.

Dosage forms can be combination dosage forms having both immediate-release and controlled-release characteristics, for example, a combination of immediate-release pellets and controlled-release pellets. The immediate-release portion of a combination dosage form may be referred to as a loading dose.

Certain compositions described herein may be "coated". The coating may be a suitable coating, such as, a functional or a non-functional coating, or multiple functional or non-functional coatings. By "functional coating" is meant to include a coating that modifies the release properties of the total composition, for example, a sustained-release coating. By "non-functional coating" is meant to include a coating that is not a functional coating, for example, a cosmetic coating. A non-functional coating can have some impact on the release of the active agent due to the initial dissolution, hydration, perforation of the coating, etc., but would not be considered to be a significant deviation from the non-coated composition.

The solid complexes of quinine sulfate and the compositions disclosed herein are useful for example to treat or for the prophylaxis of malaria caused by *Plasmodium* species (e.g., *falciparum, vivax*, and the like), uncomplicated *Plasmodium falciparum* malaria, severe or complicated *Plasmodium falciparum* malaria; the treatment or prophylaxis of leg muscle cramps (e.g., nocturnal recumbency leg muscle cramps), and the treatment of babesiosis caused by *Babesia microti*.

Malaria is a parasitic disease caused by the *Plasmodium* species *P. falciparum, P. vivax, P. ovale* and *P. malariae*. Malaria parasites are transmitted by female *Anopheles* mosquitoes. Without being held to theory, it is believed that quinine toxic to the malaria parasite, specifically by interfering with the parasite's ability to break down and digest hemoglobin, thus starving the parasite or causing the build-up of toxic levels of partially degraded hemoglobin.

Nocturnal recumbency leg muscle cramps, a common complaint in the elderly, is manifested as painful, involuntary contractions in the lower extremities after recumbency. Quinine can be used for the treatment of leg cramps including those associated with arthritis, diabetes, varicose veins, thrombophlebitis, arteriosclerosis and static foot deformities.

Babesiosis is caused by *Babesia microti*. The definitive host is a tick, in this case the deer tick, *Ixodes dammini* (*I. scapularis*). Humans enter the cycle when bitten by infected ticks; during a blood meal, a *Babesia*-infected tick introduces sporozoites into the human host.

The following examples further illustrate the invention but, of course, should not be construed as in any way limiting its scope.

EXAMPLES

X-ray powder diffraction analyses are performed on an Inel XRG-3000 diffractometer, equipped with a curved position-sensitive detector with a 2-theta range of 120°. Real time data is collected using Cu Ka radiation at a resolution of 0.03° 2-theta. The tube voltage and amperage are set to 40 kV and 30 mA, respectively. Samples are prepared for analysis by packing them into thin-walled glass capillaries. Each capillary is mounted onto a goniometer head that is motorized to permit spinning of the capillary during data acquisition. Instrument calibration is performed daily using a silicon reference standard. Peak lists are generated by using FileMonkey v3.2.0, Notepad v5.1, Dash v3.1, EXCEL 2003, and PatternMatch 2.3.6. The XRPD patterns are background-corrected and prominent peaks are selected with the following parameters in Dash v3.1 (wavelength 1.541874 Å, 15 iterations, 150 window, Monte Carlo, Smooth w/5 window). Peak positions are rounded to the nearest 0.1° 2-theta, relative intensities are rounded to the nearest 1%, peaks with a relative intensity less than 10% are removed, and peaks above 26° 2θ are also removed.

Differential scanning calorimetry (DSC) analyses is carried out on a TA Instruments differential scanning calorimeter 2920; calibrated using indium reference. The sample is placed in a standard aluminum DSC pan with an uncrimped lid. The sample cell is equilibrated at 0° C. and heated under nitrogen purge at a rate of 10° C./minute up to a final temperature of 300° C.

Thermogravimetry (TG) analyses are carried out on a TA Instruments 2950 thermogravimetric analyzer. The calibration standards are nickel and Alumel™. Each sample is place in an aluminum sample pan and inserted into the TG furnace. Samples are started at ambient and then heated under a stream of nitrogen at a heating rate of 10° C./min, up to a final temperature of 175 or 350° C.

Fourier Transform Raman (FT-Raman) spectra are obtained using a FT-Raman 960 spectrometer (Thermo Nicolet) using an excitation wavelength of 1064 nm. Approximately 0.3 W of Nd:YVO$_4$ laser power is used to irradiate the sample. The Raman spectra are measured with a germanium (Ge) detector. The samples are prepared for analysis by placing the material in a glass tube and positioning the tube in a gold-coated tube holder in the accessory. A total of 256 sample scans are collected from 3600-100 cm$^{-1}$ at a spectral resolution of 4 cm$^{-1}$, using Happ-Genzel apodization. Wavelength calibration is performed using sulfur. Data are analyzed and peak lists are generated by using Omic v. 7.2 software.

Example 1

Preparation of Quinine Sulfate/Bisulfate Solid Complexes: Manual Screen

The specific parameters of the manual screen studies are provided in Table 1 below. Generalized procedures for the preparation of the solid complexes are provided below.

A generalized milling process involves placing approximately equal amounts of quinine sulfate and respective guest compounds into an agate milling holder with a milling ball for milling at ambient temperature. The sample is dry milled. The sample is milled for specific time intervals (2 and 20 minutes) at 30 Hz using a Retsch MM200 mixer mill. The vial is opened and solids scraped from the side of the milling holder and ball in 5 minutes increments for the 20 minute grinding experiments.

Antisolvent Crystallization (AC). Solutions are prepared in various solvents at ambient temperatures and filtered through a 0.2-μm nylon filter. Antisolvent is then added and the solution is allowed to stand at ambient.

Ambient Crystallization (AmC). Solutions are prepared in various solvents at ambient temperatures and filtered through a 0.2-μm nylon filter. The solutions are then allowed to stand at ambient.

Crash Cool (CC). Solutions are prepared in various solvents at elevated temperatures and filtered through a 0.2-μm nylon filter into a vial. Vials are then either left at ambient or placed in the refrigerator or a freezer.

Liquid Diffusion (LD). Solutions were prepared and filtered through a 0.2-μm nylon filter. The filtered solution was allowed to diffuse into an antisolvent in a small glass tube at ambient temperature. The anti-solvent used is miscible with the solvent and the tubes are left vertically and undisturbed at ambient.

Slow Cool (SC). Solutions are prepared using various solvents at elevated temperatures and filtered through a 0.2-μm nylon filter into an open vial while still warm. The vial is allowed to cool slowly to room temperature. The presence or absence of solids is noted. If there are no solids present, or if the amount of solids is judged too small for XRPD analysis, the vial is placed in a refrigerator. Again, the presence or absence of solids is noted and if there were none, the vial was placed in a freezer. Solids that formed are isolated by filtration and allowed to dry prior to analysis.

Slow Evaporation (SE). Solutions are prepared in various solvents and sonicated between aliquot additions to assist in dissolution. Once a mixture reaches complete dissolution, as judged by visual observation, the solution is filtered through a 0.2-μm nylon filter. The filtered solution is allowed to evaporate at ambient in a vial covered with aluminum foil perforated with pinholes.

Slurry. Solutions are prepared by adding enough solids to a given solvent so that excess solids are present. The mixture is then agitated in a sealed vial at ambient.

All isolated solids are analyzed by X-ray powder diffraction revealing new XRPD patterns.

TABLE 1

| Guest | Solvent | Ratio API:guest | Method | XRPD result Description |
|---|---|---|---|---|
| Acetic acid | Acetone | — | Antisolvent precipitation | Acetic acid cocrystal monohydrate White solid, small needles |
| Acetic acid | — | — | Milling/20 minutes | Acetic acid cocrystal monohydrate White solid |
| Acetic acid | — | — | Milling/20 minutes | Acetic acid cocrystal monohydrate Off-white solid, irregular particles |
| DL-Tartaric acid | Ethanol | 2:1 | Slow cool (~70° C. to freezer) | Quinine bisulfate tartaric acid cocrystal White solid, thin needles |
| DL-Tartaric acid | Ethanol | 2:1 | Complete dissolution followed by precipitation and slurry at ~70° C. | Quinine bisulfate tartaric acid cocrystal + peaks White solid, irregular particles |
| DL-Tartaric acid | Ethanol | 2:1 | Complete dissolution followed by precipitation and slurry at ~70° C. | Quinine bisulfate tartaric acid cocrystal Off-white solid, irregular particles |

Example 2a

Preparation of Quinine Sulfate Acetic Acid Solid Complex-Milling

About 103 milligrams (mg) of quinine sulfate is milled with 20 microliters of glacial acetic acid in a ceramic sample holder for 20 minutes on a ball mill. Off-white solids are obtained and analyzed by XRPD, $^1$H NMR, Elemental analysis, and DSC (Table 2).

TABLE 2

| Analytical Technique | Results |
|---|---|
| XRPD | Quinine sulfate acetic acid cocrystal monohydrate |
| $^1$H NMR | Similar to quinine sulfate 0.5 moles of acetic acid per mole of quinine |
| Elemental Analysis | Experimental: 60.18 (% C); 6.76 (% H); 6.64 (% N); 3.97 (% S) Theoretical: 61.15 (% C); 6.84 (% H); 6.79 (% N); 3.89 (% S) Composition: Quinine sulfate•acetic acid•$H_2O$ |
| DSC | Endotherms: 93° C., 213° C. (onset: 208° C.) |

Example 2b

Preparation of Quinine Sulfate Acetic Acid Solid Complex-Antisolvent Precipitation Approximately 4 grams of quinine sulfate is dissolved in 8 mL of acetic acid. Antisolvent acetone, 43 mL, is added and white precipitation forms upon stirring at ambient. Solids (3.5 g) are collected by vacuum filtration, followed by an air dry over night. The solids are analyzed by $^1$H NMR, DSC, and TG (Table 3); and by XRPD (FIG. 1, peak listing Table 4) and FT-Raman (FIG. 2, peak listing Table 5).

TABLE 3

| Analytical Technique | Results |
| --- | --- |
| XRPD | Quinine sulfate acetic acid cocrystal monohydrate |
| $^1$H NMR | Similar to quinine sulfate |
|  | 0.4 moles of acetic acid per mole of quinine |
| TG | 2.7% weight loss up to 120° C. |
| DSC | Endotherms: 97° C., 205° C., 213° C. |

TABLE 4

XRPD peaks

| Position (°2-theta ± 0.1 °2-theta) | I/I$_o$ relative intensity |
| --- | --- |
| 8.4 | 100 |
| 15.2 | 30 |
| 16.6 | 58 |
| 17.0 | 92 |
| 17.8 | 18 |
| 18.3 | 11 |
| 19.3 | 14 |
| 20.4 | 92 |
| 23.8 | 12 |
| 25.2 | 15 |
| 25.7 | 45 |

TABLE 5

FT-Raman peaks
Region 3600.4 to 98.3 cm−1
Absolute threshold 3.606
Sensitivity 100

| (cm$^{-1}$) | Intensity |
| --- | --- |
| 123.8 | 37.026 |
| 148.5 | 57.506 |
| 181.3 | 23.671 |
| 225.7 | 10.321 |
| 246.9 | 8.29 |
| 263.8 | 9.28 |
| 330.9 | 5.841 |
| 353.1 | 8.309 |
| 376.3 | 5.549 |
| 401 | 16.132 |
| 438.1 | 17.794 |
| 465.5 | 9.378 |
| 527.9 | 13.265 |
| 541.1 | 7.159 |
| 553.2 | 15.964 |
| 577.9 | 10.345 |
| 625.3 | 5.534 |
| 642.8 | 4.922 |
| 665.1 | 5.423 |
| 696.5 | 4.534 |
| 720.3 | 3.915 |
| 763.2 | 22.446 |
| 775.1 | 19.159 |
| 790.1 | 24.522 |
| 802.5 | 19.666 |
| 832 | 15.108 |
| 856.2 | 8.995 |
| 868.5 | 5.754 |
| 883.3 | 5.568 |
| 921.6 | 7.752 |
| 937.9 | 4.568 |
| 967.8 | 8.297 |
| 983.2 | 19.316 |
| 1007.6 | 8.918 |
| 1017.5 | 8.026 |
| 1030.4 | 7.854 |
| 1044.8 | 6.513 |
| 1056.3 | 13.306 |
| 1078.3 | 9.789 |
| 1100.2 | 7.367 |
| 1132.1 | 10.724 |
| 1146.6 | 4.041 |
| 1168.1 | 6.011 |
| 1177.9 | 8.423 |
| 1186 | 6.972 |
| 1204.8 | 10.279 |
| 1229.2 | 25.821 |
| 1241.9 | 11.058 |
| 1267.7 | 11.253 |
| 1277.9 | 10.374 |
| 1303.9 | 18.795 |
| 1312.8 | 21.092 |
| 1364 | 248.267 |
| 1404.8 | 10.043 |
| 1428.8 | 41.254 |
| 1445.3 | 40.024 |
| 1508.9 | 9.246 |
| 1574.8 | 14.812 |
| 1592.5 | 23.513 |
| 1619.9 | 19.464 |
| 1643.8 | 21.718 |
| 1726.8 | 3.796 |
| 2836.8 | 8.329 |
| 2860 | 6.294 |
| 2884.9 | 11.968 |
| 2954.3 | 59.396 |
| 2974.3 | 34.394 |
| 2992.4 | 34.988 |
| 3004.7 | 32.4 |
| 3046.1 | 22.768 |
| 3074.8 | 29.228 |

Example 2c

Preparation of Quinine Sulfate Acetic Acid Solid Complex-Single Crystal

Attempts to prepare a single crystal of quinine sulfate acetic acid solid complex are carried out in a variety of solvent systems and procedures according to Table 6 below. Single crystal structure determination was made from material prepared from liquid diffusion in ethyl acetate provides quinine sulfate acetic acid cocrystal monohydrate.

TABLE 6

| Solvent | Condition[a] | Description[b] |
|---|---|---|
| Acetone | LD | Thin needles with B and E |
| Acetone | AC | Thin needles and fibers with B and E |
| Acetone | SE | Irregular particles with B and E |
| Acetone | SE | Irregular particles and fibers with B and E |
| ACN | SE | Fibers |
| ACN | SE | Irregular Particles |
| ACN | AC | Thin needles and fibers with B and E |
| DCM | SE | Irregular particles and fibers with B and E |
| DCM | SE | Fibers with B and E |
| DCM | SC (RT to rfg) | Small particles with B and E |
| DCM | SC (RT to rfg) | Small particles with B and E |
| Dioxane | AC | Small needles with B and E |
| Dioxane | AC | Small needles with B and E |
| Dioxane | SC (RT to rfg) | Small needles with B and E |
| Dioxane | SC (RT to rfg) | Small needles with B and E |
| Dioxane | SE | Fibers with B and E |
| EtOAc | AC | Irregular Particles |
| EtOAc | AC | Irregular Particles |
| EtOAc | SE | Irregular particles and fibers with B and E |
| EtOAc | SE | Clear gel |
| EtOAc | AC | Thin needles and fibers with B and E |
| EtOAc | LD | Needles with B and E |
| EtOAc | LD | Long needles with B and E |
| EtOAc | LD | Long needles with B and E |
| EtOAc | LD | Long needles with B and E |
| EtOAc | LD | Long needles with B and E |
| EtOAc | LD | Long needles with B and E |
| Nitromethane | SE | Fibers with B and E |
| Nitromethane | SE | Fibers with B and E |
| THF | AC | Irregular Particles |
| THF | AC | Irregular Particles |
| THF | AC | Small needles with B and E |
| THF | AC | Small needles with B and E |
| THF | SC (RT to rfg) | Small needles with B and E |
| THF | SC (RT to rfg) | Small needles with B and E |
| Toluene | SE | Fibers with B and E |
| Toluene | SE | Fibers with B and E |
| Toluene | Slurry/RT | Brown oil |

[a]SE = slow evaporation, SC = slow cool, AC = antisolvent crystallization, LD = liquid diffusion, RT = room temperature, rfg = refrigerator
[b]B = birefringence, E = extinction Example 3a Preparation of Quinine Bisulfate Tartaric Acid Solid Complex About 100 mg of quinine sulfate and 38 mg of tartaric acid (1:2) are completely dissolved in 1.0 ml of ethanol at about 70° C. Precipitation formed and the mixture is allowed to slurry on a stir plate overnight. Off-white solids (30 mg) are collected by vacuum filtration and analyzed by XRPD, $^1$H NMR, Elemental analysis, and DSC (Table 7).

TABLE 7

| Analytical Technique | Results |
|---|---|
| XRPD | Quinine bisulfate tartaric acid cocrystal |
| $^1$H NMR | Chemical structure of quinine appears intact 0.9 mole of DL-tartaric acid per mole of quinine |

TABLE 7-continued

| Analytical Technique | Results |
|---|---|
| Elemental Analysis | Experimental: 50.42 (% C); 5.55 (% H); 4.66 (% N); 5.65 (% S); Theoretical: 50.34 (% C); 5.63 (% H); 4.89 (% N); 5.60 (% S) Composition: Quinine bisulfate•tartaric acid |
| DSC | Broad exotherm: 75° C. Endotherm: 200° C. (onset 195° C.) |

Example 3b

Large Scale Preparation of Quinine Bisulfate Tartaric Acid Solid Complex

Figure 4:
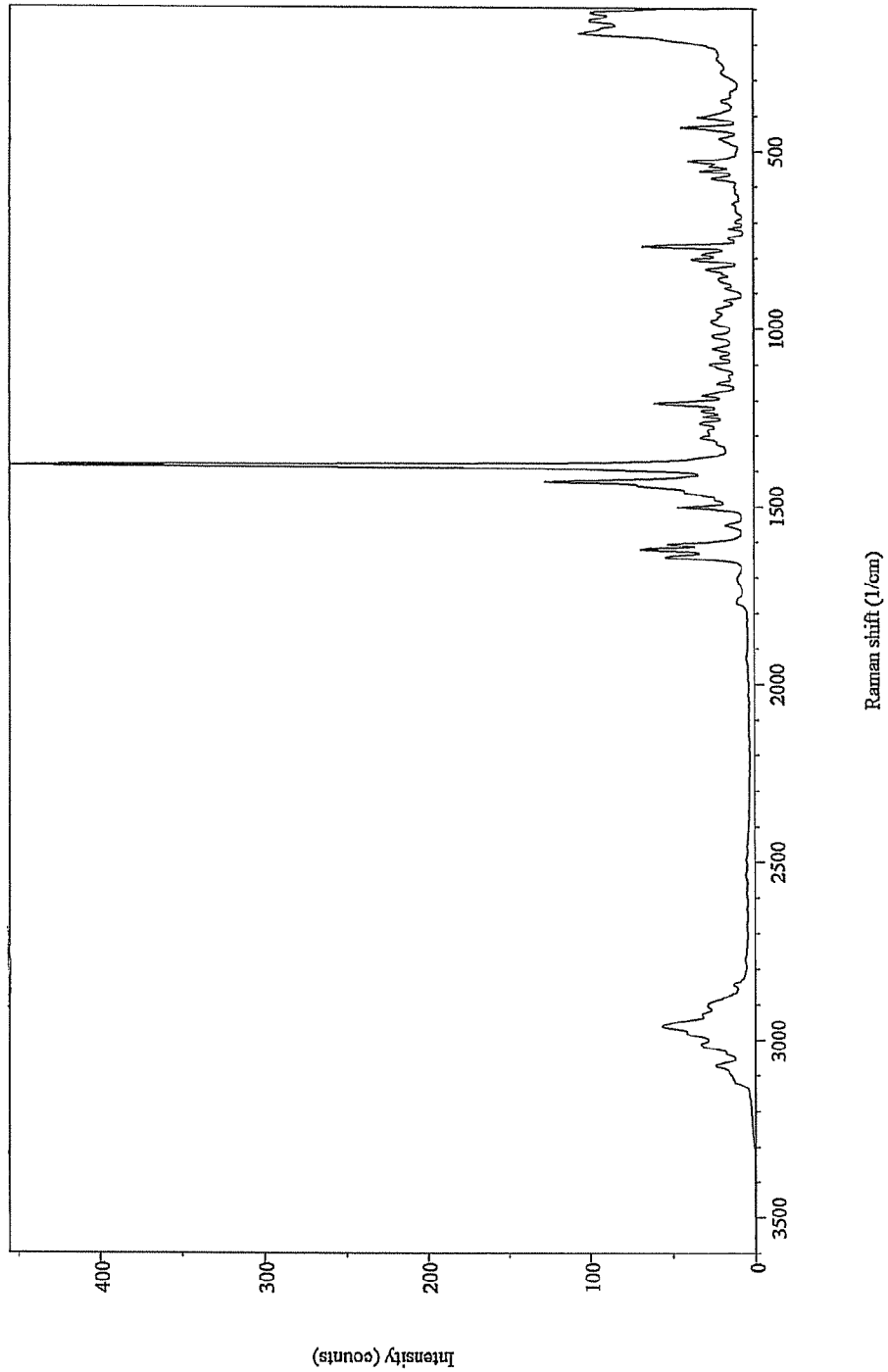
FIG. 4 illustrates FT-Raman spectrum of quinine bisulfate tartaric acid solid complex.

Approximately 5 grams of quinine sulfate and 1.9 gram of tartaric acid (1:2) were completely dissolved in 50 mL of hot ethanol (~70° C.). Precipitation formed upon stirring at ~70° C. over night. Solids (2.8 g) are then collected by vacuum filtration. The material is then further dried in a vacuum oven at room temperature for 4 days. $^1$H NMR, DSC, and TG analyses are performed (Table 8). The solids are analyzed by XRPD (FIG. 3, peak listing Table 9) and FT-Raman (FIG. 4, peak listing Table 10).

TABLE 8

| Analytical Technique | Results |
|---|---|
| XRPD | Quinine bisulfate tartaric acid cocrystal |
| TG | 1.4% weight loss up to 80° C. |
| $^1$H NMR | Chemical structure of quinine appears intact 0.9 mole of tartaric acid per mole of quinine 0.1 mole of ethanol |
| TG | 1.1% weight loss up to 70° C. |
| DSC | Endotherms: 63° C., 192° C. |

TABLE 9

| XRPD peaks | |
|---|---|
| Position (°2-theta ± 0.1 °2-theta) | I/I$_o$ relative intensity |
| 9.4 | 53 |
| 10.4 | 28 |
| 13.8 | 17 |
| 15.2 | 17 |
| 15.6 | 34 |
| 16.8 | 42 |
| 17.4 | 100 |
| 18.7 | 50 |
| 19.5 | 85 |
| 20.0 | 16 |
| 20.5 | 30 |
| 20.7 | 25 |
| 21.6 | 18 |
| 22.8 | 25 |
| 23.3 | 12 |
| 24.0 | 24 |
| 24.6 | 13 |
| 25.7 | 16 |

TABLE 10

FT-Raman peaks
Region 3600.4 to 98.3 cm−1
Absolute threshold 8.828
Sensitivity 100

| (cm$^{-1}$) | Intensity |
|---|---|
| 111 | 99.392 |
| 133.2 | 99.909 |
| 169.5 | 106.089 |
| 240.2 | 22.174 |
| 277.5 | 19.294 |
| 335.1 | 14.144 |
| 358 | 19.104 |
| 404.1 | 34.553 |
| 432.9 | 44.957 |
| 464.5 | 20.302 |
| 503.1 | 10.467 |
| 528.8 | 39.555 |
| 540.8 | 26.865 |
| 555.4 | 32.47 |
| 576.3 | 25.619 |
| 598 | 11.638 |
| 613.7 | 11.159 |
| 632.7 | 8.934 |
| 646.9 | 12.792 |
| 661.1 | 10.464 |
| 668.5 | 10.43 |
| 696.5 | 11.231 |
| 717.3 | 15.219 |
| 743.6 | 15.375 |
| 767 | 68.064 |
| 790.1 | 31.741 |
| 804.5 | 37.417 |
| 831.9 | 29.316 |
| 844 | 18.927 |
| 859.3 | 21.095 |
| 885.6 | 17.242 |
| 919 | 17.646 |
| 945.5 | 22.74 |
| 979.2 | 25.831 |
| 1019 | 25.493 |
| 1055.1 | 25.074 |
| 1079.5 | 20.105 |
| 1099.7 | 26.919 |
| 1132.1 | 15.194 |
| 1153.4 | 22.046 |
| 1186.9 | 31.809 |
| 1210 | 60.663 |
| 1231.3 | 32.378 |
| 1246.5 | 31.26 |
| 1265.4 | 32.966 |
| 1288.3 | 27.932 |
| 1305.5 | 32.834 |
| 1322.9 | 22.557 |
| 1386.4 | 455.802 |
| 1431.1 | 127.991 |
| 1442.1 | 71.226 |
| 1502.8 | 46.972 |
| 1552.6 | 17.441 |
| 1606.4 | 52.475 |
| 1621.7 | 68.89 |
| 1642.6 | 53.877 |
| 1703.9 | 10.479 |
| 1769.3 | 11.013 |
| 2844.1 | 13.271 |
| 2860.4 | 11.149 |
| 2900.7 | 29.204 |
| 2928.8 | 32.758 |
| 2962.1 | 56.771 |
| 2980.8 | 41.561 |
| 3011.8 | 33.653 |
| 3035.3 | 17.744 |
| 3071 | 24.63 |
| 3114.9 | 12.743 |

Example 3c

Preparation of Quinine Bisulfate Tartaric Acid Solid Complex-Single Crystal

Attempts to prepare a single crystal of quinine bisulfate tartaric acid solid complex are carried out in a variety of solvent systems and procedures according to Table 11 below.

TABLE 11

| Solvent | Condition | Description |
|---|---|---|
| EtOH/MeOH | Crash cool ~70 C. to room temp., slow evaporation room temp. | Clustered blades |
| EtOH/MeOH | Crash cool ~70 C. to room temp., fast evaporation room temp. | Chunks |
| MeOH* | Slow cool ~70 C. to room temp. | Blades, some clustered |

*50 mg quinine bisulfate/tartaric acid cocrystal and 26 mg DL-tartaric acid are dissolved in hot methanol.

Single crystal analysis of material obtained from crystallization in methanol reveals the material is a quinine bisulfate tartaric acid cocrystal.

The terms "comprising", "having", "including", and "containing" are to be construed as open-ended terms (i.e., meaning "including, but not limited to"). The terms "a" and "an" do not denote a limitation of quantity, but rather denote the presence of at least one of the referenced item. The term "or" means "and/or". The endpoints of all ranges directed to the same component or property are inclusive and independently combinable.

Unless defined otherwise, technical and scientific terms used herein have the same meaning as is commonly understood by one of skill in the art to which this invention belongs.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Figure 2:
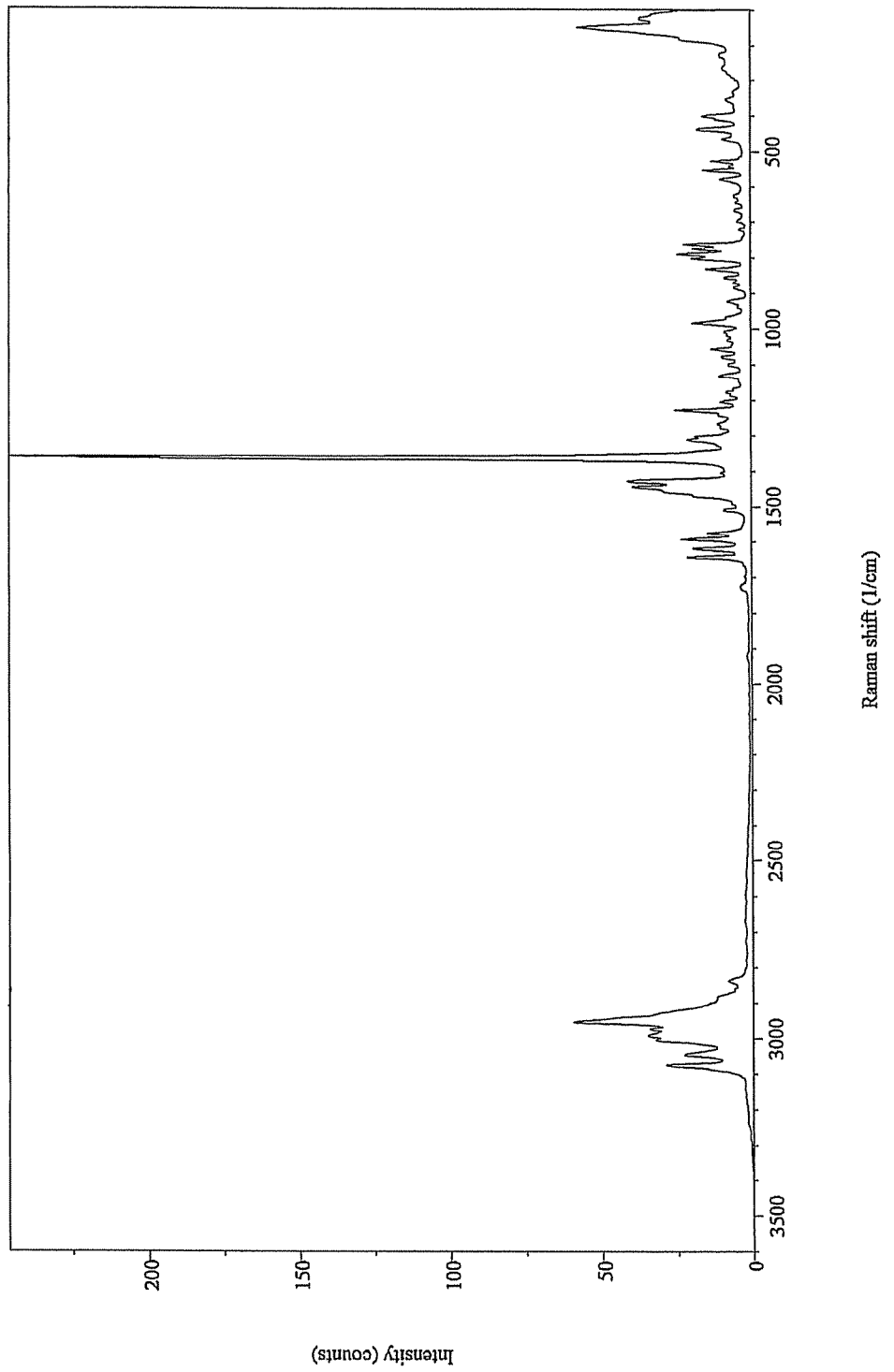
FIG. 2 illustrates FT-Raman spectrum of quinine sulfate acetic acid solid complex.

What is claimed is:

1. Quinine sulfate acetic acid solid complex comprising one or more of the following:

XRPD peak positions at 8.4, 15.2, 16.6, 17.0, 17.8, 19.3, 20.4, 23.8, 25.2, and 25.7±0.1 degree 2-theta;

XRPD peak positions as in Table 4;

an X-ray powder diffraction pattern as in FIG. 1;

FT-Raman peaks at 1364, 1429, 1445, and 2954±4 cm$^{-1}$;

FT-Raman peaks substantially as in Table 5; or

FT-Raman spectrum as in FIG. 2.

2. The solid complex of claim 1, wherein the solid complex is quinine sulfate acetic acid co-crystal monohydrate.

3. Quinine bisulfate tartaric acid solid complex comprising one or more of the following:
   XRPD peak positions at 9.4, 10.4, 13.8, 15.2, 15.6, 16.8, 17.4, 18.7, 19.5, and 20.5±0.1 degrees 2-theta;
   XRPD peak positions as in Table 9;
   an X-ray powder diffraction pattern as in FIG. 3;
   FT-Raman peaks at 767, 1386, 1431, and 1622±4 cm$^{-1}$;
   FT-Raman peaks as in Table 10; or
   FT-Raman spectrum as in FIG. 4.

4. A composition, comprising:
   the quinine sulfate acetic acid solid complex of claim 3 or the quinine bisulfate tartaric acid solid complex of claim 3; and
   a pharmaceutically acceptable excipient.

5. The composition of claim 4, wherein the composition is a solid oral dosage formulation.

6. A method of treating a patient in need of quinine therapy, comprising:
   administering to a patient in need thereof the solid complex of claim 1 or claim 3.

7. A method of treating a patient in need of quinine therapy, comprising:
   administering to a patient in need thereof the composition of claim 4.

8. The method of claim 6, wherein the solid complex is used to treat malaria caused by *Plasmodium* species, uncomplicated *Plasmodium falciparum* malaria, severe or complicated *Plasmodium falciparum* malaria, malaria caused by *Plasmodium vivax*, leg muscle cramps, or babesiosis; or for the prophylaxis of malaria or leg muscle cramps.

9. The method of claim 7, wherein the composition is used to treat malaria caused by *Plasmodium* species, uncomplicated *Plasmodium falciparum* malaria, severe or complicated *Plasmodium falciparum* malaria, malaria caused by *Plasmodium vivax*, leg muscle cramps, or babesiosis; or for the prophylaxis of malaria or leg muscle cramps.

10. A method of preparing the solid complex of claim 1, comprising one of the following:
   i.) milling a combination of quinine sulfate and acetic acid to form quinine sulfate acetic acid solid complex;
   ii) preparing quinine sulfate acetic acid solid complex by liquid diffusion in ethyl acetate; or
   iii) adding an anti-solvent to a solution containing quinine sulfate, a guest, and optionally a solvent system; and precipitating a quinine sulfate solid complex, wherein the guest is acetic acid.

11. A method of preparing the solid complex of claim 3, comprising one of the following:
   i) crystallizing a solid complex from a solution containing quinine sulfate, a guest, and optionally a solvent system with optionally evaporating the solvent system from the solution, wherein the guest is DL-tartaric acid; or
   ii) dissolving quinine sulfate and tartaric acid in a lower alkyl alcohol with heating, and allowing the solid complex to precipitate.

12. The method of claim 11, wherein i) further comprises seeding the solution.

13. The method of claim 10, wherein the anti-solvent of iii) is acetone.

14. The method of claim 10, wherein iii) further comprises slurrying the quinine sulfate, guest, and solvent system.

15. The solid complex of claim 1 comprising XRPD peak positions at 8.4, 15.2, 16.6, 17.0, 17.8, 19.3, 20.4, 23.8, 25.2, and 25.7±0.1 degree 2-theta.

16. The solid complex of claim 1 comprising an X-ray powder diffraction pattern as in FIG. 1.

17. The solid complex of claim 3 comprising XRPD peak positions at 9.4, 10.4, 13.8, 15.2, 15.6, 16.8, 17.4, 18.7, 19.5, and 20.5±0.1 degrees 2-theta.

18. The solid complex of claim 3 comprising an X-ray powder diffraction pattern as in FIG. 3.

* * * * *